July 16, 1957 H. M. TIRET Plant Pat. 1,621
FUCHSIA PLANT
Filed Oct. 5, 1956
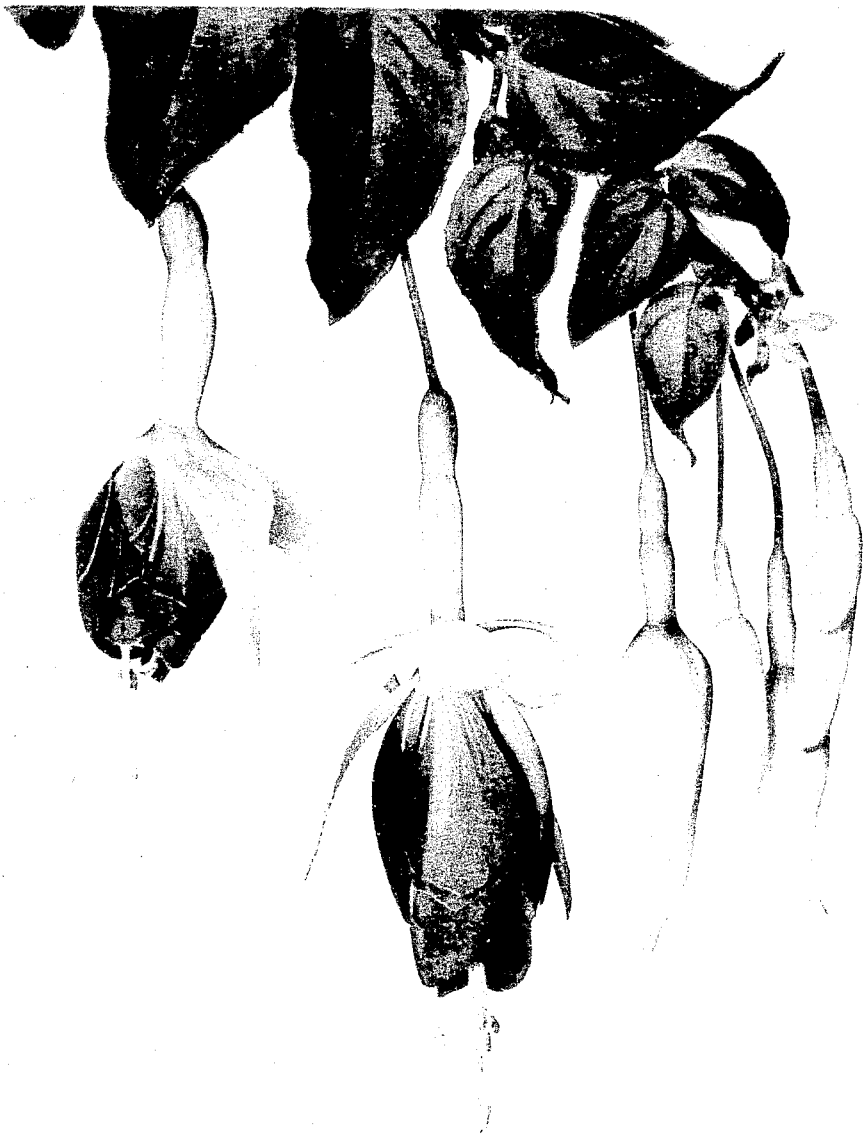

United States Patent Office

Plant Pat. 1,621
Patented July 16, 1957

1,621

FUCHSIA PLANT

Horace M. Tiret, San Francisco, Calif.

Application October 5, 1956, Serial No. 614,331

1 Claim. (Cl. 47—60)

This invention relates to a new and improved fuchsia plant, the principal new and different characteristic of which is the contrasting color and form composed of the Cardinal Red corolla and white sepals and tube, in a semi-trailer plant.

As a hybrid from a seedling (unpatented) not introduced to the trade, namely 7–57–24 and San Francisco (unpatented), the figures representing applicant's own breeding symbols, the plant has been asexually reproduced at Colma, California and Gardena, California, by cuttings which retained the characteristics of the parent fuchsia.

The plant is a semi-trailer and grows vigorously. It is very self-branching with extremely long, colorful and contrasting flowers. The flowers are produced in abundance. It is an early bloomer.

In the accompanying drawing, the figure shows a typical branch tip; the drawing representing approximate actual size.

A detailed description of this new variety of fuschia plant follows:

*Habit of growth.*—Vigorous, semi-trailing variety. Blooms early.

*Foliage.*—Medium in size, dark green in color. Leaves are lightly veined with edges serrated to a medium degree. Branches are greenish-brown. The mature leaf is approximately 2¾″ in length and 1⅝″ in width at the widest point.

*Petals.*—The petals are flushed white near the base, otherwise Cardinal Red (British Horticultural Chart #822/3) which is the predominant color. When the flower first opens the petals are Chrysanthemum Crimson (British Horticultural Chart #824/3) becoming Cardinal Red at maturity.

The petals number approximately 20, lying close together in an overlapping manner. The corolla is long, compact and tapering. The diameter of the mature flower is approximately 1¼″. Length of the large petals is 1⅝″, width 1¾″ (spread out). Appearance of the petals is smooth.

*Ovary.*—Solid green in color. Lenth ½″, width at widest point 5/16″, when flower is fully open.

*Tube.*—Long and slender. Length approximately 1¼″, width at widest point ¼″. White with greenish cast.

*Sepals.*—Topside is white with a greenish cast. Tips are Pea Green (British Horticultural Chart #61/1). Underside is white. Sepals are slender in form, and curl back against tube. They are four in number, 2″ in length and ⅝″ in width at widest point. Outerside, smooth and satiny, underside, crepelike in appearance.

*Stamens.*—Eight in number, white with flesh colored anthers. Slender, length 2¼″.

*Pistil.*—The style is approximately 3½″ in length and 1/32″ in width. It is white in color, while the stigma is creamy white.

*Buds.*—White in color with green tips. Length from ovary is approximately 2⅝″, and width at widest point is ¾″, creating a slender effect.

*Parentage.*—Applicants own seedling (unpatented) not introduced to the trade, applicant's breeding symbol 7–57–24, and San Francisco (unpatented).

Having thus disclosed my discovery, I claim:

A new and distinct variety of fuchsia plant herein described, characterized by the Cardinal Red corolla and white sepals and tube, combined with the unusual form and vigorous, semi-trailing habit of growth, resulting in an appearance unlike any fuchsia of its type.

No references cited.